(12) United States Patent
Maleti

(10) Patent No.: US 10,722,364 B2
(45) Date of Patent: Jul. 28, 2020

(54) PROSTHETIC VALVE FOR TREATING DISEASES CAUSING REFLUX AFFECTING THE LOWER LIMBS

(71) Applicant: Oscar Maleti, Modena (IT)

(72) Inventor: Oscar Maleti, Modena (IT)

(*) Notice: Subject to any disclaimer, the term of this patent is extended or adjusted under 35 U.S.C. 154(b) by 433 days.

(21) Appl. No.: 15/356,303

(22) Filed: Nov. 18, 2016

(65) Prior Publication Data

US 2017/0065417 A1 Mar. 9, 2017

Related U.S. Application Data

(63) Continuation of application No. PCT/IB2015/053555, filed on May 14, 2015.

(30) Foreign Application Priority Data

May 21, 2014 (IT) .............................. RM2014A0257

(51) Int. Cl.
*A61F 2/24* (2006.01)
*A61F 2/06* (2013.01)

(52) U.S. Cl.
CPC .......... *A61F 2/2475* (2013.01); *A61F 2/2418* (2013.01); *A61F 2002/065* (2013.01); *A61F 2210/0004* (2013.01); *A61F 2220/0075* (2013.01)

(58) Field of Classification Search
CPC ...... A61F 2/2475; A61F 2/856; A61F 2/2418; A61F 2002/061; A61F 2002/065
See application file for complete search history.

(56) References Cited

U.S. PATENT DOCUMENTS

| 8,403,979 B2* | 3/2013 | Paul, Jr. .............. A61F 2/2412 623/1.24 |
| 2005/0228486 A1 | 10/2005 | Case et al. |
| 2008/0183280 A1 | 7/2008 | Agnew et al. |
| 2008/0288055 A1 | 11/2008 | Paul et al. |
| 2009/0254176 A1* | 10/2009 | Butera .................. A61F 2/2418 623/1.24 |
| 2014/0222144 A1* | 8/2014 | Eberhardt ............. A61F 2/2418 623/2.38 |

FOREIGN PATENT DOCUMENTS

EP 2 105 110 A1 9/2009

OTHER PUBLICATIONS

Bauer et al., "The Etiology of Leg Ulcers and Their Treatment by Resection of the Popliteal Vein," *J. Int. Chir.* 8:937-967 (1948).
Bauer et al., Division of Popliteal Vein in the Treatment of So-Called Varicose Ulceration; *British Medical* Journal, 2(4674):318-321 (Aug. 5, 1950).

(Continued)

*Primary Examiner* — Brian A Dukert
(74) *Attorney, Agent, or Firm* — Klarquist Sparkman, LLP

(57) ABSTRACT

The present invention relates to a monocusp prosthetic valve comprising a flap made of biocompatible material, and a stent made of biocompatible or bio-absorbable material, said stent having meshes defining holes with profile represented by any closed curve or polygonal shape, wherein in said prosthetic valve the flap is sewn on said stent by means of pairs of suture points that are longitudinally extended along opposite surfaces of said flap.

8 Claims, 6 Drawing Sheets

(56) References Cited

OTHER PUBLICATIONS

Kistner, "Surgical Repair of a Venous Valve," *Straub Clinic Proceedings,* 34(2):41-43 (1968).
Kistner et al., "Surgery in Acute and Chronic Venous Disease," *Surgery,* 85(1):31-43 (Jan. 1979).
Linton et al., "Postthrombotic Syndrome of the Lower Extremity—Treatment by Interruption of the Superficial Femoral Vein and Ligation and Stripping of the Long and Short Saphenous Veins," *Surgery,* 3:452-468 (Sep. 24, 1948).
Linton, "The Post-Thrombotic Ulceration of the Lower Extremity: its Etiology and Surgical Treatment," *Annals of Surgery,* 138(3):415-433 (Sep. 1958).
Taheri et al., "Surgical Treatment of Postphlebitic Syndrome with Vein Valve Transplant," Abstract of *AM. J. Surgery,* 144(2):221-224 (Aug. 1982).

* cited by examiner

PROSTHETIC VALVE FOR TREATING DISEASES CAUSING REFLUX AFFECTING THE LOWER LIMBS

CROSS-REFERENCE TO RELATED APPLICATIONS

This application is a continuation of international patent application PCT/IB2015/053555, filed on May 14, 2015, designating the U.S., which international patent application has been published in the English language and claims priority from Italian patent application RM2014A000257, filed on May 21, 2014. The entire contents of these priority applications are incorporated herein by reference.

BACKGROUND OF THE INVENTION

The present invention refers to the medical field. More in detail the present invention refers to a new prosthetic valve to be implanted in the venous system, typically of the lower limbs, adapted to allow a physiological blood flow where such flow has been altered by diseases causing a reflux affecting the lower limbs. The venous system of the lower limbs represents a complex system, constituted by a deep district formed by the satellite veins of the arteries, a superficial system represented by the saphenae and their branches, a system of interconnection between the two constituted by the perforating veins and by a rich network of intramuscular veins that are particularly important with regard to the rear leg muscles. Each of these systems can generate physiopathological alterations such to determine a significant chronic venous insufficiency scenario.

The disease of the deep venous system is particularly serious, both with regard to difficult treatment and the fact that actions taken to confront associated superficial system and perforating vein diseases have extremely temporary effect. The venous system of the lower limbs in fact acts as a single entity, and the alteration of one sector is generally transmitted to the others. In particular, it is known that large-size varices can cause an expansion of the deep venous system with relative incompetence of the valves thereof, returning to size and function only after correction of the varices themselves. In other words, this is a reversible functional insufficiency of the deep venous system due to an overload by the superficial system. The reverse interconnection is the expansion of the superficial system due to a deep reflux through the expansion of the perforating veins. The ligature of the latter leads to temporary results, since the disease of the depth is capable of continuously expanding other perforating veins.

Hence, the reflux disease affecting the lower limbs is to be examined by investigating the entire venous system and the treatment aimed towards correcting the deep system, if pathological. In general, a reflux affecting the deep venous system originates from alterations of the structure which physiologically prevents reflux, i.e. the valve. Valves are either congenitally altered or they have acquired such alteration. Congenital alteration can consist of poor functioning, as an altered structure, or absence of the valve itself: poor functioning is the most common form. Given that the valve is constituted by two intimal flaps arranged with their opening upward, in a manner so as to form sacks such to prevent the anti-physiological flow of the venous flow, it may happen that these flaps do not carry out their containment function and allow the blood flow in both directions. This possibility is termed primary valve insufficiency. In other occasions, the flaps are present but hypotrophic; in other cases, much rarer, they are atrophic and hence entirely absent. These scenarios generally determine a serious form of chronic venous insufficiency, already present in youth, and in addition they can be complicated during life with the superimposition of phlebothrombosis. The alteration of the valves of acquired type instead derives from the lesion thereof by a thrombotic process, and therefore this is part of the post-thrombotic syndrome. The post-thrombotic syndrome, much more frequent than congenital forms, originates from the rechanneling by endogenous fibrinolysis processes with extended phlebothrombosis affecting the deep venous system. The veins can reacquire their axial permeability but generally the valves result completely damaged and incorporated in a parietal thickening process of fibrotic type. The size of the reflux, generally associated with alteration of the superficial venous system and of the perforating veins, generates scenarios of severe chronic venous insufficiency, with appearance of relapsing ulcers. When a chronic venous insufficiency is controllable with operations affecting the superficial venous system or corrections of perforating veins associated with physical aids (elastic sock), the presence of deep venous reflux can be tolerated. In specific cases, nevertheless, significant and disabling symptoms can suggest a surgical operation aimed for correcting the deep reflux itself. The importance of deep venous reflux in the genesis of alterations of trophism of the limb was already known to Linton in 1931, who suggested as correction the ligature of the femoral vein, thus introducing the concept that an obstructed flow was preferable to the reflux itself. Along the same lines, Bauer in 1955 suggested the ligature of the popliteal vein: the patients subjected to this treatment did not report severe complications, rather they improved their conditions, but nearly all of them relapsed due to the formation of side effects in turn refluent that rendered the ligature inefficient. Heart valve surgery instead has much more recent origins; it arose in fact due to Kistner who in 1968 executed the first human heart valve operation. This case was one of primary valve insufficiency. Kistner's operation, subsequently modified by others, still remains the operation commonly executed for this type of disease: after having identified with echo color doppler and phlebography the seat of a valve nest, where a non-functioning valve is present, an operation is conducted that provides for a direct access to the valve itself through a phlebotomy. The usually prolapsed valve flaps are stressed and stretched upward, in order to re-give them a correct morphology and a certain functionality. This is a delicate operation, to be conducted with great care. Most results are particularly encouraging and the healing of refractory trophic lesions occurs in most cases.

Nevertheless, the operation reconstructs only one valve within the venous axis, so that it is still necessary to employ complementary actions in post-operative stage (deambulation, elastic constriction, anti-edema devices), in order to maintain the homeostasis of the limb. If Kistner's operation is capable of correcting congenital valve disease, the same is however not applicable in the congenital forms of hypotrophy and atrophy and in the acquired forms of post-thrombotic type. In order to correct these forms, and in particular those of post-thrombotic type due to their high frequency, two operation types have been proposed: the first by Kistner in 1978, femoral transposition, and the other by Taheri in 1982, autograft.

Transposition is an interesting operation that consists of sectioning the superficial femoral vein and of anastomosis of the distal fragment on the deep femoral vein or on the saphena upstream of a competent valve.

This is a fascinating, well-functioning operation which, however, in over half the patients, cannot be conducted. The main reason consists of the fact that the deep femoral vein is also often incompetent in its first section and that the saphena is either incompetent or often absent due to previous removal.

The autograft proposed by Taheri consists of drawing, from the arm, a section of axillary vein which has a competent valve and its subsequent implant with end-end anastomosis in popliteal vein. It is necessary to ascertain beforehand that the axially vein contains a functioning valve; nevertheless, the size discrepancy and the reluctance of the patient to accept limitations of the upper limb render this operation one of rare application.

The creation of a neovalve by executing a parietal dissection is a further possibility, but this is a surgical operation executed in only a few centers and in limited numbers.

Research leading to a corrective action, when the above-described operations cannot be conducted, have led to the creation of various techniques, including: the reduction of the femoral vein size, the implant of cryopreserved valves and the implant of valves on stents.

The first two methods did not provide satisfactory results, while the implant of valves on stents is still in experimental phase.

In particular, the valves designed up to now have presented unsatisfactory experimental and clinical studies due to two main factors: malfunctioning of the valve and thrombosis in the valve nest.

Before commencing the description of the present invention, it should be observed that in physiology, the valve is not inserted within a cylindrical section having the same size at the valve itself, and above and below such valve, but rather it is inserted at a physiological expansion of the vessel, which is termed valve nest. The significance of this physiological expansion was recently well-documented by in vivo studies executed with B-Flow technique, which show that an ascending flow—through a decrease of speed thereof and consequent creation of return forces capable of acting in latero-medial direction on the valve—cause the closing of such valve. More clearly, the valves are situated in an intermediate position between the opening and closing and are closed by the same flow through forces that can only be exerted by virtue of the morphology of the valve nest itself.

None of the valve on stent designs made up to now have considered this important rule and therefore the valve does not work correctly, its valve nest is not washed by a flow, so that the valve remains in an immobile position and the valve nest precociously develops thrombosis.

At this point, there are essentially two possibilities foreseen for overcoming this great obstacle: creating a stent that reproduces the physiological expansion of the venous nest and inserting the new valve at this expansion, or overcoming the thrombosis and immobility in another manner. In particular the most important characteristics that a valve device must satisfy are the following: mobility (the valve must be movable and not fixed) and the fact that the valve nest, i.e. the nest comprised between the valve itself and the venous wall, is washed by the blood circulation. Since this washing action is exerted by the return of blood, and given that this return is not present since there is no expansion of the venous nest, the object of the present industrial invention patent application, described in detail hereinbelow, is to propose a new device that meets both the valve mobility requirement and the possibility of washing the valve nest.

It should be indicated that the valve mobility derives from opposite forces on the valve flap and given that there is no flow within the valve nest, the flap remains practically immobile, except for occasional forces that exert a counter-current flow. It is also opportune to specify that an anti-reflux action can be exerted by a valve mechanism formed by a valve with two flaps (bicuspid) or three flaps (tricuspid) or one flap (monocusp). The fact that the monocusp exerts an effective anti-reflux action, equal to a bicuspid or a tricuspid, has allowed attaining the definition of the present object, described hereinbelow.

It is important to specify that the valves are situated below the tributary veins, i.e. side branches that are inserted along the main venous axis and the main flow allows, during the speed slowing and accelerations thereof, the emptying of the tributary veins themselves through suction mechanisms and speed accelerations (Venturi effect). Physiological valves do not have tributary veins that arise directly from the venous nest whose washing, as stated above, is represented by the return circulation of the ascending flow. The awareness of these aspects has allowed designing and obtaining, with the aid of mathematical models, a valve device capable of restoring the physiological blood flow for use in treating the abovementioned diseases.

SUMMARY OF THE INVENTION

The present description refers to a new and innovative device to be used in the medical field for obtaining a valve which is movable and which has a nest suitably washed by the blood current. More clearly, the present description refers to a valve device shaped as a monocusp valve, hence formed by only one flap, sewn on a stent. All this defines a highly innovative valve designed and specifically attained for its insertion seat.

The present valve is in fact suitably designed for being positioned not in a continuous parietal section, as has always been suggested, but rather across from a collateral vein such as a large tributary vein. In this manner, the large tributary vein will maintain the valve nest continuously washed, thus avoiding the risk of thrombosis. The present valve allows preventing reflux. The large tributary vein maintains the valve flap open, pushing it towards the counter-lateral wall. This spatial configuration of the flap ensures the anti-reflux action, given that a possible thrust of blood from above would exert its full force in the open flap towards the counter-lateral wall, and the blood would be directed towards the tributary vein which, provided with functioning valves, would stop the reflux here. The risk that the valve flap pushed against the counter-lateral wall represents an obstacle for the normal flow of the pathological vein is also avoided, as the mathematical models used for the simulation of the functioning of the present valve have shown.

More in detail, the mathematical models have shown that the total occlusion of this vein, determined by the flow at the tributary vein, is only temporary. The occlusion determines a pressure increase at the main vein itself and such pressure increase will open the valve, allowing normal flow. The mathematical model also shows that the main vein and the tributary vein thus develop a competitive flow that can be exactly overlapped on the physiological flow that is attained between the main axis and the tributary vein. In addition, in the application of the valve, the tributary vein originates from the valve nest and not far therefrom.

Thus, the attainment of a monocusp valve suitably designed for its insertion across from a collateral vein such as a large tributary vein fully accomplishes the object of washing the valve nest, thus preventing thrombosis, and obtaining a movable flap. It is also important to specify that the new valve flap, following the implant of the valve, maintains positions that allow the normal flow of the tributary vein within the main axis and which prevent the reflux each time that it is manifested. This is obtained with a simple and particular system of sewing the valve on the stent. All of this with the result of maintaining the flap in permanent semi-open position, preventing both the twisting and the malfunctioning thereof.

The material useful for attaining the valve is preferably bovine pericardium, already widely used for attaining heart valves with transcutaneous insertion, but other biocompatible materials can also be used. Therefore, by joining two structures that are already widely tested and used, such as a stent and a biological tissue, localizing all this exactly across from the emergence of a large tributary vein and sewing the flap in a specific manner on the stent, it was possible to obtain a valve meeting the hemodynamic needs of venous physiology and that allows treating diseases that cause blood reflux affecting the lower limbs. The stent is preferably a structure with wide meshes, which is therefore such to prevent any obstacle of the blood flow.

DESCRIPTION OF PREFERRED EMBODIMENTS

Figure 1:
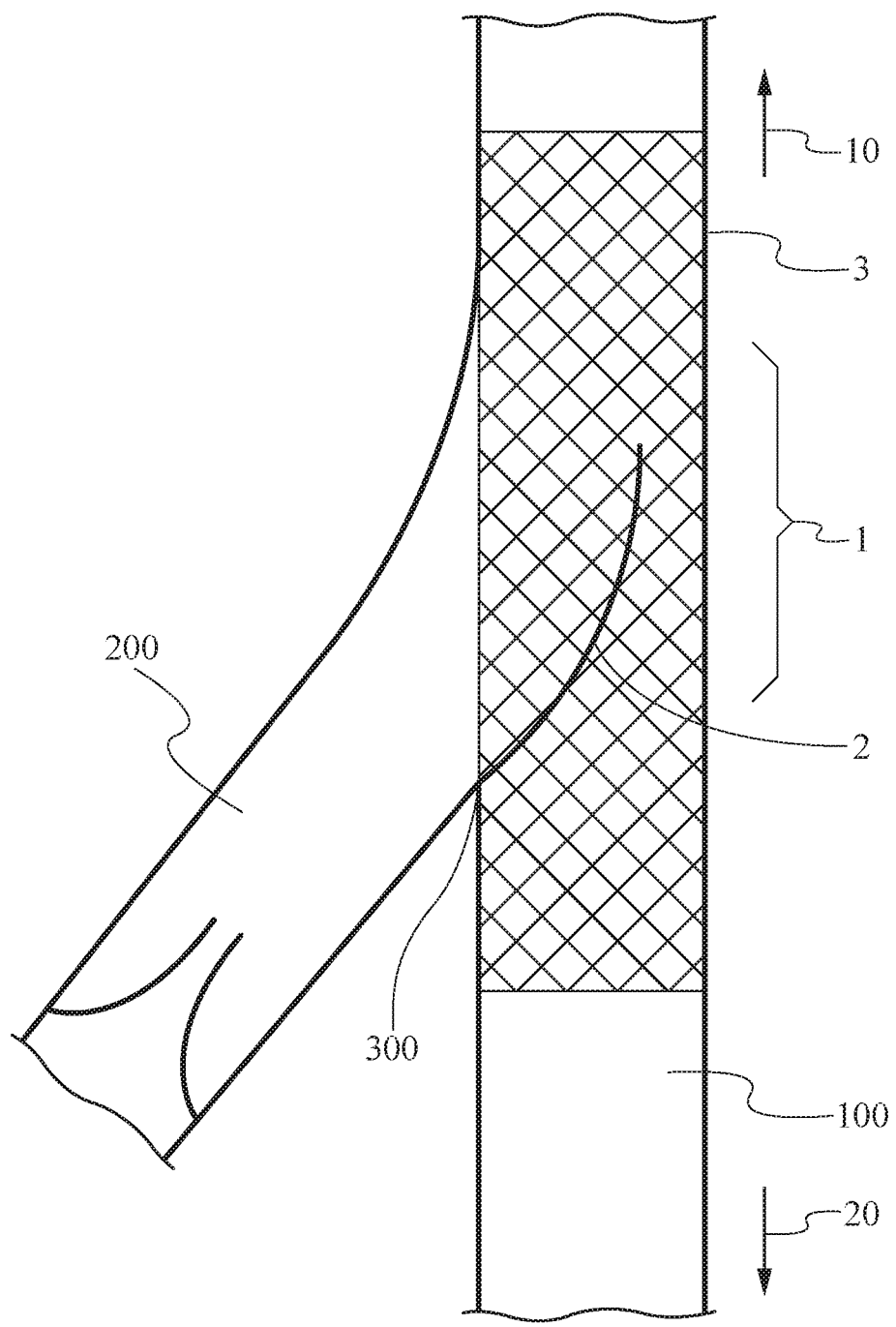
FIG. 1 shows a schematic view of the prosthetic valve 1, subject of the present industrial invention patent application. The figure in question intends to show that said valve 1, comprising the flap 2 and the stent 3, is sized, shaped and spatially configured for being inserted in a vein 100 at the height of the junction 300 between said vein 100 and a collateral vein 200. The references represented by the arrows 10 and 20, in the figure in question, respectively indicate the direction of the vein 100 in the direction of the heart and feet. The figure also shows that the stent 3 is formed by meshes 3' which define holes 3" with rhomboid profile.
Figure 2:
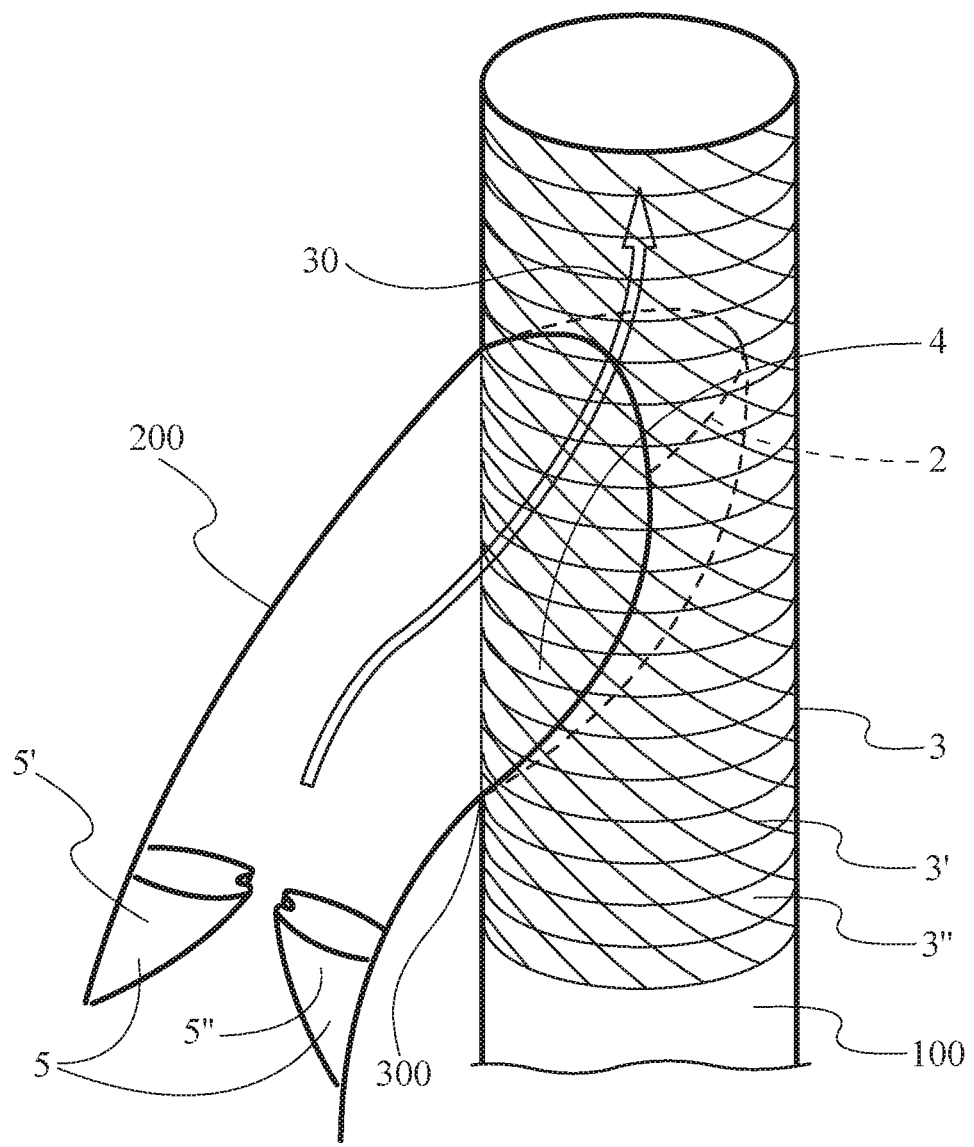
FIG. 2 shows a perspective view of the vein 100 with the prosthetic valve 1 implanted at its interior at the height of the junction 300 with the collateral vein 200. The figure in question intends to underline the direction of the blood flow of the vein 200. Said direction of the flow is represented by the arrow 30. As can be understood from observing the figure, the direction of the flow indicated with the arrow 30 allows maintaining the valve nest 4, defined by the flap 2, continuously washed, thus preventing the formation of blood pooling within said nest 4 and consequent formation of thrombi. The figure also shows the presence of the physiological valve 5 comprising the valve nests 5' and 5" of the collateral vein 200. Said valve 5 functions correctly.
Figure 3:
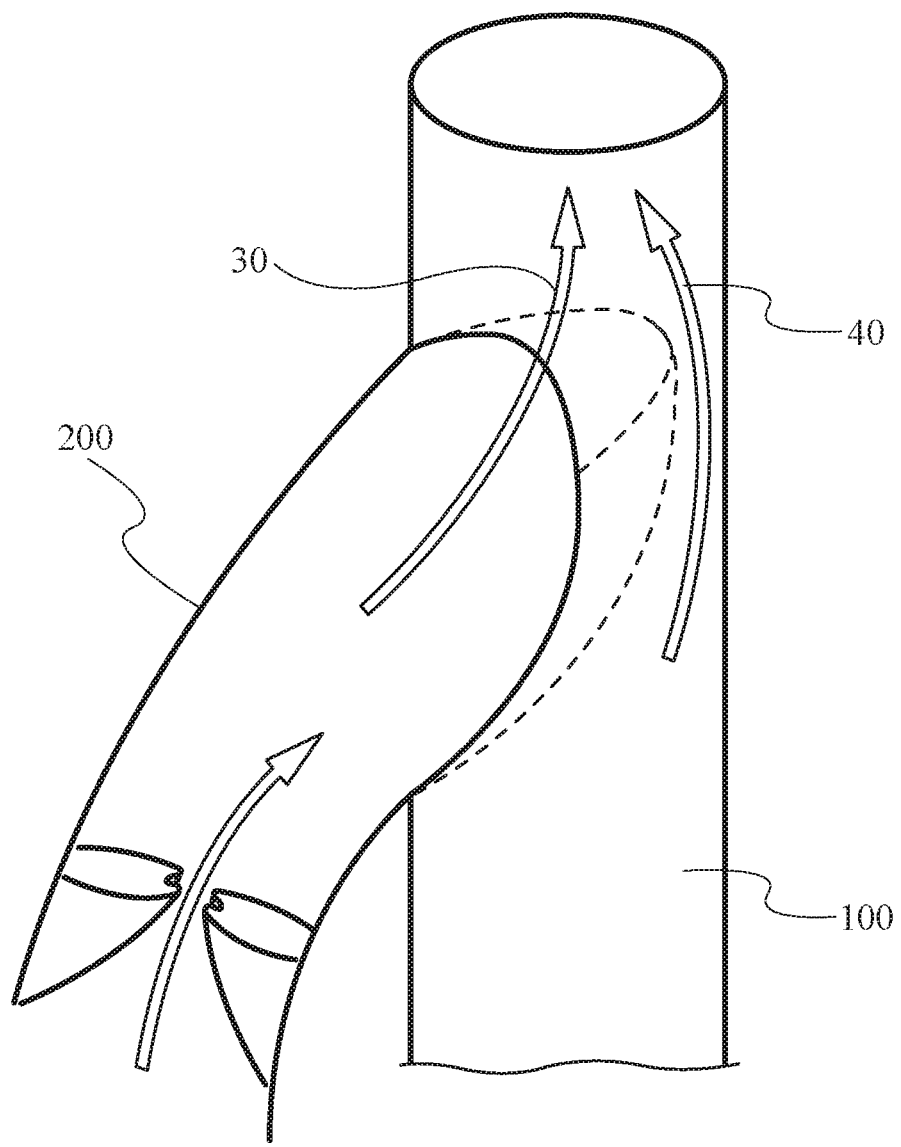
FIG. 3 is similar to FIG. 2 but intends to underline the mobility of the flap 2, of the prosthetic valve 1, caused by the blood flows represented by the arrows 30 and 40 which respectively indicate the direction of the blood flow coming from the collateral vein 200 and from the vein 100.
Figure 4:
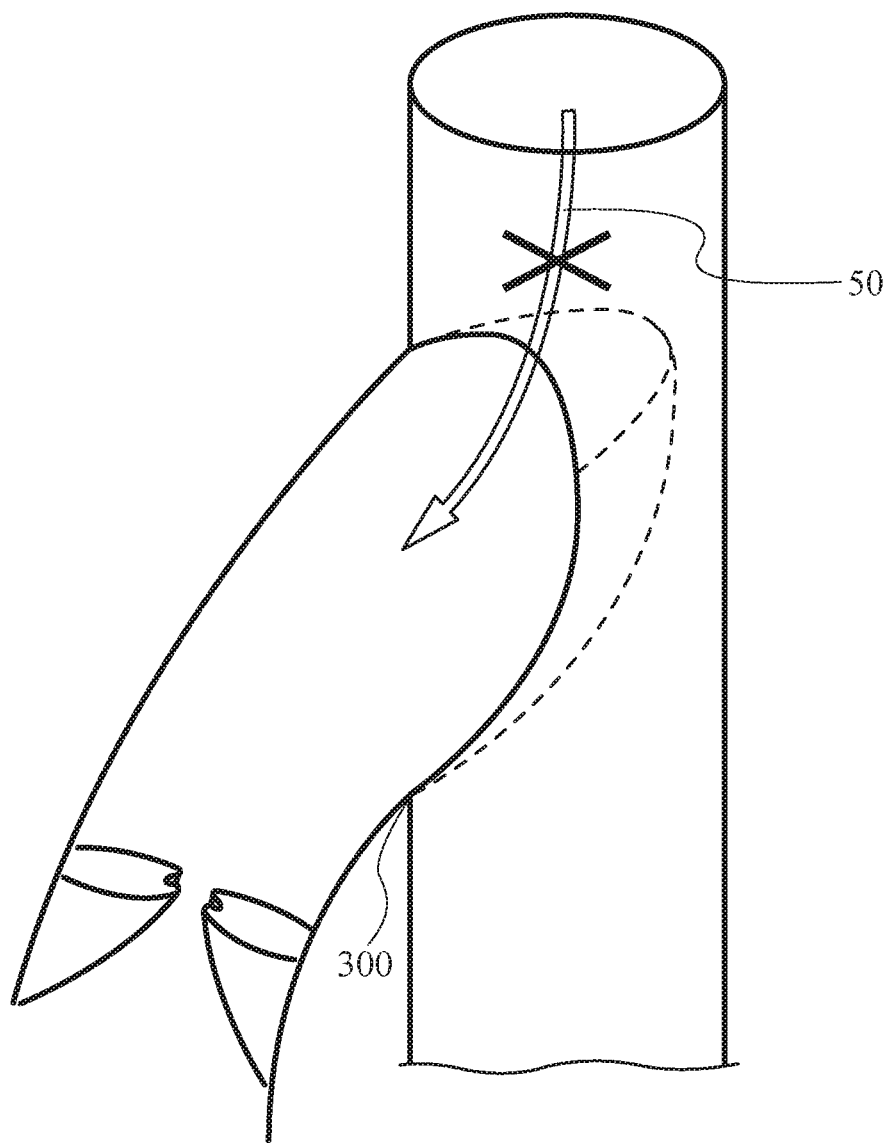
FIG. 4 is similar to the preceding FIGS. 2 and 3 but intends to underline the absence of blood reflux, represented by the direction of the arrow 50, due to the implant of the prosthetic valve 1 at the height of the junction 300.
Figure 5:
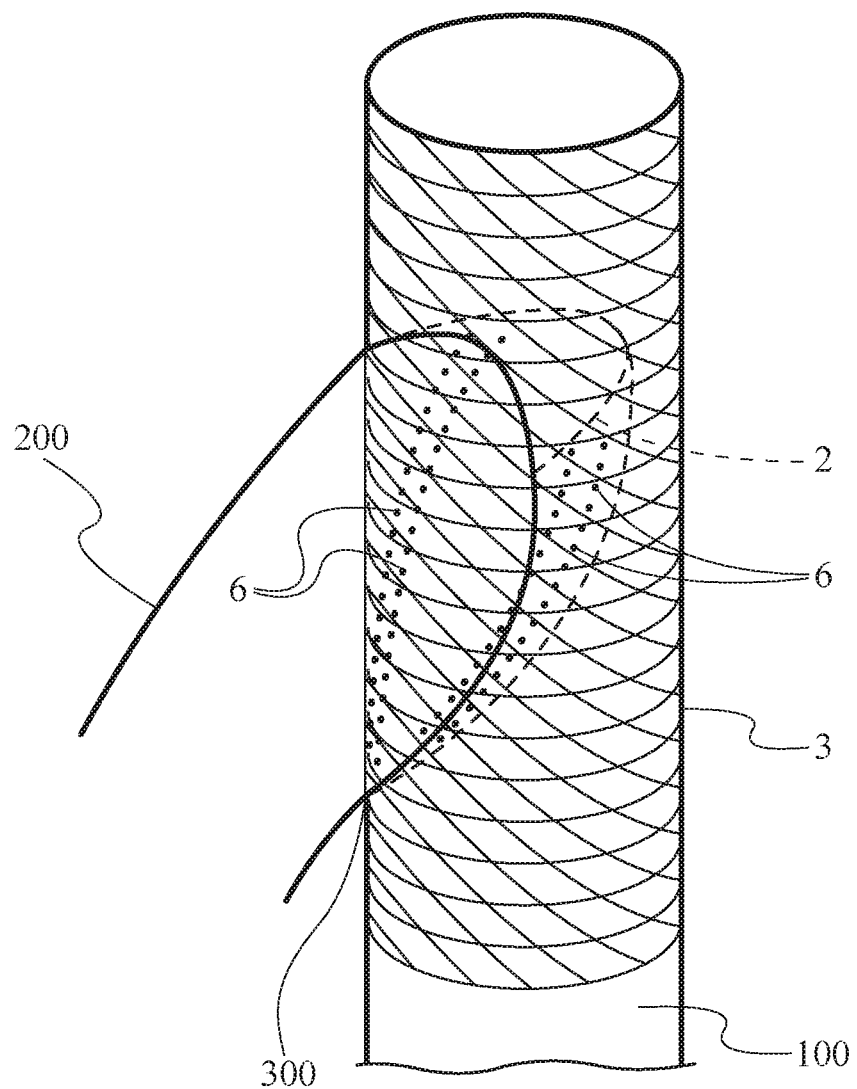
FIG. 5 shows a perspective view of the implant of the prosthetic valve 1 within the vein 100 at the height of the junction 300. The figure intends to show that the flap 2 of said valve 1 is sewn on the stent 3. The sewing is particular and is represented by a plurality of pairs 6 of suture points, longitudinally extended along opposite surfaces of the flap 2.
Figure 6:
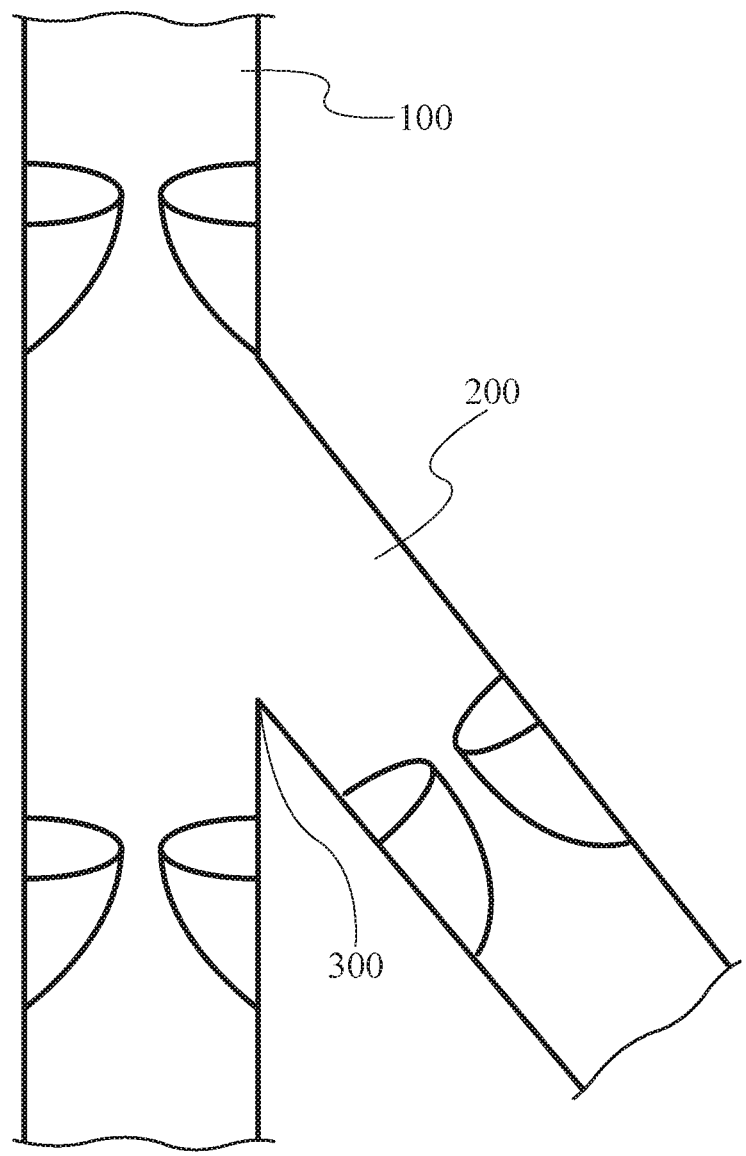
FIG. 6 shows a schematic view of a normal vein 100, joined to a vein 200, in which the physiological valves present therein are observable. The figure intends to show that the physiological valves, in addition to being bicuspid valves, contrary to the present prosthetic valve 1 which is represented by a monocusp, cannot be found at the height of the junction 300.

As anticipated multiple times in the course of the present description, the subject of the invention is a new prosthetic valve 1 to be implanted in subjects having diseases that cause blood reflux. More in detail, the present industrial invention patent application describes a prosthetic valve 1 suitably designed and obtained for preventing both the reflux and the risk of thrombosis caused by blood pooling, which is inevitably produced in the valve nest itself. The present prosthetic valve 1 also comprises a flap 2 whose mobility does not alter the physiological blood flow within the venous district. All this occurs while avoiding the risk of blood reflux. The attainment of the aforesaid objects has been obtained by defining a valve 1 suitably shaped and sized for its implant at a collateral vein 200 such as a large tributary vein. More specifically, the prosthetic valve 1, subject of the present invention, is a monocusp valve that comprises a flap 2 made of biocompatible material which is specifically sewn on a stent 3, also suitably designed for imparting, to said valve 1, the necessary characteristics for attaining the object of the invention.

Still more in detail, the valve 1 is such to be spatially configured at the junction 300 between a collateral vein 200 and a vein 100 in which the blood flow is altered by valve dysfunctions also at points that can be relatively far from the implant zone of the prosthetic valve 1. The valve 1, implanted in this specific junction zone, is such that its flap 2 and the venous nest 4 defined by said flap 2 are continuously washed by the blood flow coming from the collateral vein 200.

By way of example, considering a vein 100 and a collateral vein 200 joined to said vein 100, the implant of the prosthetic valve 1 is to be executed at the junction 300 of the two veins. The valve flap 2 thus extends in the direction of the blood flow within the vein 100 and defines a valve nest 4 that is continuously washed by the blood flow coming from the collateral vein 200. In this spatial configuration, the valve flap 2 assumes conformation such to have a correct mobility which is, in turn, capable of ensuring the physiological blood flow within the vein 100 and the absence of reflux within the same vein 100. The risk of reflux is in fact prevented not only by the normal blood flow within the vein 100, facilitated by the mobility of the new flap 2, but also by the thrust exerted by the blood flow of the tributary vein 200 that has correctly functioning valves at its interior.

As already mentioned, the effectiveness of the correct functioning of the prosthetic valve 1 has already been verified by utilizing mathematical models. In particular the simulations obtained were detected by means of Fluid-Structure-Interaction (FSI) analysis. For the blood and for the structural characteristics of the valve 1, the following parameters were assumed:

Blood:
    Density: 1060 Kg/m3
    Dynamic viscosity: 0.035 Poise
    Newtonian flow Ignored dependence of the viscosity on the speed or pressure
Isotropy Structural Characteristics of the Valve:

For the materials tested in the mathematical model, structural criticalities were not encountered. In addition, the fluid-dynamic functioning scheme resulted coherent with the expectations.

A non-limiting example is reported hereinbelow of the characteristics of a particular embodiment of the prosthetic valve 1 when said valve 1 is to be implanted within a vein with diameter variable from 6 to 20 mm.

Stent:
material: nitinol
weight: from 1 to 4 g, e.g. 2.5 g
average diameter of the holes 3" defined by the meshes 3': from 3 mm to 5 mm, e.g. 4 mm.
profile of the holes 3" defined by the meshes 3' of the stent 3: rhomboidal
profile of the cross section of the meshes 3': rectangular or circular Flap:
material: bovine pericardium, ovine pericardium, swine pericardium or other biocompatible material Valve:
length of the valve: from 1.5 to 2.5 cm, e.g. 2 cm.
Radius of curvature at its maximum point: from 3 to 10 mm, e.g. 5.5 mm.

It should be indicated that, in other embodiments, the present prosthetic valve 1 has structural characteristics adapted to enhance the effectiveness of its implant. In particular, some embodiments provide that the stent 3 is made of a biocompatible and bio-reabsorbable material comprising, by way of a non-limiting example, materials such as polylactic acids (PLA), polyglycolic acids (PGA) and polydioxanone (PDS) and/or that the profile of the holes 3"—defined by the meshes 3' of the stent 3, which can be represented by any closed curve or polygonal shape, analogous to the cross section of the same meshes defining the stent 3—is elliptical.

By way of a non-limiting example, a particular embodiment of the present prosthetic valve 1 provides that the holes 3" have an elliptical profile, and that the cross section of the meshes 3' has circular profile.

What is claimed is:

1. A method for treating a pathology that causes a reflux affecting the lower limbs, wherein the method comprises implanting into a patient in need thereof a monocusp prosthetic valve, the monocusp prosthetic valve comprising a flap made of biocompatible material, and a stent made of biocompatible or bio-absorbable material, said stent having meshes defining holes with profile represented by any closed curve or polygonal shape, wherein in said prosthetic valve the flap is sewn on said stent by pairs of suture points that are longitudinally extended along opposite surfaces of said flap, wherein the method comprises implanting the monocusp prosthetic valve in a vein at a height of a junction between said vein and a collateral vein.

2. The method as claimed in claim 1, wherein the cross section of the meshes of the stent of the monocusp prosthetic valve is defined by any closed curve or polygonal form.

3. The method as claimed in claim 1, wherein the holes defined by the meshes of the stent of the monocusp prosthetic valve have a rhomboid profile.

4. The method as claimed in claim 1, wherein the holes defined by the meshes of the stent have a rhomboid profile while the cross section of said meshes is rectangular.

5. The method as claimed in claim 1, wherein the flap is made of bovine pericardium, ovine pericardium or swine pericardium while the stent is made of nitinol.

6. The method as claimed in claim 1, wherein the flap is made of bovine pericardium, ovine pericardium or swine pericardium while the stent is made of bio-reabsorbable material, said bio-reabsorbable material being a polylactic acid (PLA), polyglycolic acid (PGA) or polydioxanone (PDS).

7. The method as claimed in claim 1, wherein the length of the average diameter of the holes varies between 3 mm and 5 mm, that the length of said valve is comprised between 1.5 cm and 2.5 cm and that its radius of curvature, measured at its maximum point, is comprised between 3 mm and 10 mm.

8. The method as claimed in claim 7, wherein the length of the average diameter of the holes is 4 mm, that the length of said valve is 2 cm and that its radius of curvature, measured at its maximum point, is 5.5 mm.

\* \* \* \* \*